United States Patent [19]

Marcelin et al.

[11] 4,365,095

[45] Dec. 21, 1982

[54] PROCESS FOR HYDROGENATING UNSATURATED COMPOUNDS

[75] Inventors: George Marcelin, Pittsburgh; Roger F. Vogel, Butler; Harold E. Swift, Gibsonia, all of Pa.

[73] Assignee: Gulf Research & Development Company, Pittsburgh, Pa.

[21] Appl. No.: 289,538

[22] Filed: Aug. 3, 1981

[51] Int. Cl.$^3$ .................. C07C 45/62; C07C 29/14; C07C 5/03

[52] U.S. Cl. .................. 568/462; 568/881; 585/276; 585/270

[58] Field of Search .................. 568/462, 881, 462; 585/276, 270

[56] References Cited

U.S. PATENT DOCUMENTS 3,278,605 10/1966 Kawasaki et al. .................. 568/462
4,018,831 4/1977 Bowes et al. .................. 568/462
4,080,311 3/1978 Kehl .................. 568/462

FOREIGN PATENT DOCUMENTS 736074 8/1955 United Kingdom .................. 568/462

*Primary Examiner*—Bernard Helfin
*Attorney, Agent, or Firm*—Deane E. Keith; Forrest D. Stine; Joseph J. Carducci

[57] ABSTRACT

A process for hydrogenating an unsaturated organic compound which comprises contacting the same with hydrogen in the presence of a catalyst composed of a support containing (1) (A) a Group IIB metal compound selected from the group consisting of zinc and cadmium compounds, (B) a combination of said zinc and cadmium compounds or (C) a combination of at least one of said Group IIB metal compounds with at least one Group IIA metal compound selected from the group consisting of magnesium, calcium, strontium and barium compounds, (2) alumina and (3) aluminum phosphate and carrying nickel thereon.

19 Claims, No Drawings

PROCESS FOR HYDROGENATING UNSATURATED COMPOUNDS

BACKGROUND OF THE INVENTION

1. Field of the Invention

The present invention relates to a process for hydrogenating an unsaturated organic compound which comprises contacting the same with hydrogen in the presence of a catalyst composed of a support containing (1) (A) a Group IIB metal compound selected from the group consisting of zinc and cadmium compounds, (B) a combination of said zinc and cadmium compounds or (C) a combination of at least one of said Group IIB metal compounds with at least one Group IIA metal compound selected from the group consisting of magnesium, calcium, strontium and barium compounds, (2) alumina and (3) aluminum phosphate carrying nickel thereon.

2. Description of the Prior Art

A support similar to that employed herein is disclosed and claimed in U.S. patent application Ser. No. 289,539 of R. F. Vogel and G. Marcelin, entitled Catalytic Supports With Controlled Pore Properties, filed concurrently herewith. The support is alleged to be useful in combination with certain metals for increasing the gasoline yield and quality from gas oils during a cracking process and additionally in catalytically cracking petroleum residues with high selectivity for gasoline production as well as possessing improved metals tolerance.

SUMMARY OF THE INVENTION

We have found, unexpectedly, that when unsaturated compounds are subjected to hydrogenation in contact with a catalyst composed of support containing (1) (A) a Group IIB metal compound selected from the group consisting of zinc and cadmium compounds, (B) a combination of said zinc and cadmium compounds or (C) a combination of at least one of said Group IIB metal compounds with at least one Group IIA metal compound selected from the group consisting of magnesium, calcium, strontium and barium compounds, (2) alumina and (3) aluminum phosphate, said support carrying nickel thereon, effective nickel utilization as high, or higher, than when conventional supports are used as carriers, is obtained. In fact, when the support components are present in the preferred ranges, nickel utilization is substantially higher than with nickel catalysts on conventional supports.

The support used herein will be composed of (1) (A) A Group IIB metal compound selected from the group consisting of zinc and cadmium compounds, (B) a combination of said zinc and cadmium compounds or (C) a combination of at least one of said Group IIB metal compounds with at least one Group IIA metal compound selected from the group consisting of magnesium, calcium, strontium and barium compounds, (2) alumina and (3) aluminum phosphate, wherein the Group IIB metal compound, including any Group IIA metal compound, is present in an amount ranging from about 0.5 to about 50 mole percent, preferably from about two to about 35 mole percent, alumina in an amount ranging from about three to about 65 mole percent, preferably from about 15 to about 60 mole percent and aluminum phosphate in an amount ranging from about 15 to about 95 mole percent, preferably from about 25 to about 80 mole percent, and having an average pore radius of from about 10 Å to about 300 Å, preferably from about 50 Å to about 200 Å, a surface area ranging from about 80 $m^2/g$ to about 250 $m^2/g$, and a pore volume of from about 0.3 cc/g to about 350 $m^2/g$, preferably from about 125 $m^2/g$ to about 250 $^2/g$, and a pore volume o from about 0.3 cc/g to about 1.5 cc/g, preferably from about 0.5 cc/g to about 1.2 cc/g. Preferably the support can be characterized after calcination at 500° C. for ten hours as being amorphous. Preferred combinations of Group IIB and Group IIA metals are zinc and magnesium and zinc and calcium. The support will carry on the surface thereof, including the surfaces within the pores, a selected amount of nickel oxide and will constitute the catalyst used herein. The amount of nickel oxide carried on the support, as elemental nickel, will be in the range of about three to about 60 weight percent, preferably about five to about 25 weight percent.

The catalyst can be prepared in a number of ways, but preferably as follows. The support is initially prepared by admixing together an aqueous solution of aluminum nitrate with an aqueous solution of zinc or cadmium nitrates, or a combination thereof, or a combination of zinc and/or cadmium nitrate with one or more Group IIA nitrates selected from the group consisting of magnesium, calcium, strontium and barium nitrates, and 85 percent aqueous phosphoric acid. The Group IIB (and Group IIA, if present) metal compound-alumina-aluminum phosphate support can be conveniently precipitated from solution by the addition of ammonium hydroxide while maintaining the solution pH in the range of about 5 to 10. After the support mixture is filtered and washed with water, it can then be mixed with a suitable nickel compound, preferably a nickel salt, such as nickel carbonate, nickel nitrate, nickel acetate, nickel formate, nickel hydroxide, etc., and blended to obtain a substantially homogeneous mixture. The resulting mixture is oven dried at about 120° to about 130° C. for about 16 to about 24 hours and then finally calcined at about 250° C. to about 650° C. for about ten hours to obtain the desired support carrying nickel oxide thereon. The Group IIB, and Group IIA, if present, metal compound in the final support are generally in their oxide form. The nickel oxide deposited on the support will range in crystallite diameter from about ten to about 200 Å, but generally will be in the range of about 30 to about 100 Å. In preparing the above catalyst the Group IIB (and Group IIA, if present) metal nitrate, aluminum nitrate, phosphoric acid and nickel entities are used in molar amounts stoichiometrically corresponding to the amounts of Group IIB (and IIA if present) metal, aluminum, nickel and phosphate components present in the desired catalyst.

The process defined and claimed herein can be used to hydrogenate unsaturated organic compounds having double and/or triple bonds, particularly those having double bonds. Of these aliphatic compounds having from two to 20 carbon atoms, particularly from two to 12 carbon atoms, and aromatic compounds having from six to 20 carbon atoms, particularly from six to 12 carbon atoms, are preferred. Especially preferred for the desired hydrogenation are aldehydes. The organic compounds can be either gaseous or liquid, at ambient pressure and temperature, but preferably are liquid. Examples of compounds that can be hydrogenated herein include ethylene, cyclohexene, acetylene, butadiene, benzene, toluene, naphthalene, anthracene, 2-ethyl-2- hexenal, heptanal, citral, cyclohexanone, 3-ene-1-pentyne, etc.

In carrying out the hydrogenation herein the compound to be hydrogenated and hydrogen are passed over the catalyst at a liquid hourly space velocity, measured at ambient temperature and pressure, of about 0.1 to about 20, preferably about 1 to 12, while maintaining in the reaction zone a temperature of about 30° to about 350° C., preferably about 50° to about 200° C., a hydrogen partial pressure of about 0 to about 1500 pounds per square inch gauge (about 0.1 to about 10.5 MPa), preferably about 100 to about 500 pounds per square inch gauge (about 0.8 to about 3.5 MPa) and total pressure of about 15 to about 2000 pounds per square inch gauge (about 0.2 to about 14.0 MPa), preferably about 115 to about 600 pounds per square inch gauge (about 0.9 to about 4.3 MPa). The recovery of the desired hydrogenated species is easily effected according to conventional procedures, for example, by release of gaseous material from the reaction product and the subsequent fractionation of the desired species from the degassed reaction product.

DESCRIPTION OF PREFERRED EMBODIMENTS

A series of runs was carried out wherein a feed consisting of 15 weight percent 2-ethyl-2-hexenal and 85 weight percent 2-ethyl-1-hexanol was subjected to hydrogenation. The 2-ethyl-1-hexanol was present as diluent to inhibit excess temperature increases in the reaction zone. Other inert liquids, such as hexane, cyclohexane, decalin, methanol, ethanol, propanol, ethylene glycol, propylene glycol, etc., could be used in place of the 2-ethyl-1-hexanol. In each run approximately five milliliters of a different hydrogenation catalyst, defined hereinafter, that had been crushed and sieved to about 20 to about 40 mesh, was placed in a stainless steel tube reactor having an inner diameter of 13 mm and a length of 1000 mm. Prior to the hydrogenation, the catalyst bed was pretreated as follows. The reactor was initially brought to 300° C. while passing 28.3 liters of nitrogen per hour over the catalyst bed, after which the catalyst bed was maintained under such conditions for two hours. Over the next 100 minutes, while still maintaining the catalyst bed at 300° C., hydrogen was bled into the nitrogen stream, with increasing amounts of hydrogen and decreasing amounts of nitrogen, until at the end of the period solely hydrogen was passed over the catalyst bed. The total amount of gas during this period amounted to 28.3 liters per hour. The flow of hydrogen over the catalyst was maintained for one hour, after which the temperature of the catalyst bed was raised to 400° C., while the hydrogen was continued to be passed thereover for an additional four-hour period. Hydrogenation, as discussed below, then proceeded. Pretreatment of the catalyst need not be done as indicated above, but can be carried out by passing hydrogen over the catalyst in a substantially inert atmosphere while maintaining the temperature in the catalyst bed between about 250° to about 600° C. and a hydrogen partial pressure of about 1.0 to about 1000 pounds per square inch gauge (about 0.007 to about 7.0 MPa) for about 0.5 to about 48 hours.

The desired hydrogenation was effected by passing 33 grams of the liquid feed per hour (as measured at ambient temperature and ambient pressure), that is, at a liquid hourly space velocity of 8.0 and four liters per hour of hydrogen while maintaining the temperature of the catalyst bed at 50° C. and the hydrogen partial pressure at 100 pounds per square inch gauge (0.8 MPa). The reaction was permitted to proceed in each run for five hours. The results obtained are tabulated below in Tables I and II. In each of Examples I and II the runs were carried out using the catalyst defined hereinabove, namely, a support comprising a Group IIB metal compound, alumina and aluminum phosphate carrying nickel, whereas in each of Examples III to VI conventional, nickel-containing catalysts were used.

TABLE I

| | Example No. | |
|---|---|---|
| | I | II |
| Catalyst Support, Mole Percent | | |
| Group IIB Metal Oxide | Zn, 33 | Zn, 10 |
| Alumina | 33 | 10 |
| Aluminum Phosphate | 34 | 80 |
| Nickel Content, Wt. Percent | 20 | 20 |
| Catalyst Pore Data | | |
| Median Pore Radius, Å | 123.8 | 99.5 |
| Pore Volume, cc/g | 0.65 | 0.39 |
| Average Pore Radius, Å | 64.5 | 44.8 |
| Surface Area, m²/g | 200.1 | 175.1 |
| Pore Size Distribution, Volume Percent | | |
| 200–300 Å Radius | 22.2 | 21.7 |
| 100–200 Å Radius | 39.3 | 28.3 |
| 50–100 Å Radius | 20.1 | 15.7 |
| 40–50 Å Radius | 3.6 | 4.8 |
| 30–40 Å Radius | 3.7 | 6.4 |
| 20–30 Å Radius | 6.6 | 11.8 |
| <20 Å Radius | 4.6 | 11.5 |
| Wt. Percent 2-ethyl-2-hexenal Converted | 52 | 26 |
| Nickel Utilization | 110 | 65 |

TABLE II

| | Example No. | | | |
|---|---|---|---|---|
| | III | IV | V | VI |
| Catalyst Support | Harshaw Ni-3266 | Kieselguhr | Silica | Alumina |
| Nickel Content, Wt. Percent | 50 | 20 | 20 | 20 |
| Catalyst Pore Data | | | | |
| Median Pore Radius, Å | 55 | 25 | 103 | 67 |
| Pore Volume, cc/g | 0.29 | 0.10 | 0.85 | 0.58 |
| Average Pore Radius, Å | 45.2 | 18.8 | 64.1 | 53.0 |
| Surface Area, m²/g | 126.3 | 111.4 | 264.9 | 220.8 |
| Pore Size Distribution, Volume Percent | | | | |
| 200–300 Å Radius | 9.4 | 1.7 | 2.6 | 9.0 |
| 100–200 Å Radius | 18.4 | 5.4 | 53.3 | 22.2 |
| 50–100 Å Radius | 27.0 | 12.0 | 34.6 | 33.8 |
| 40–50 Å Radius | 11.8 | 6.4 | 2.2 | 10.7 |
| 30–40 Å Radius | 13.3 | 14.4 | 1.5 | 10.7 |
| 20–30 Å Radius | 14.1 | 15.7 | 2.4 | 10.8 |
| <20 Å Radius | 5.9 | 44.5 | 3.4 | 2.9 |
| Wt. Percent 2-ethyl-2-hexenal Converted | 50 | 9.5 | 29 | 52 |
| Nickel Utilization | 30 | 11 | 72 | 86 |

The catalysts used in Table I were prepared as follows. A first solution was prepared by dissolving 281.2 grams of aluminum nitrate [Al(NO$_3$)$_3$. 9H$_2$O] in one liter of distilled water and a second by dissolving 74.89 grams of zinc nitrate hexahydrate in one liter of distilled water. After the two solutions were combined there was added thereto 28.6 grams of 85 percent aqueous phosphoric acid. There was then prepared a 1:1 volume mixture of water and ammonium hydroxide (containing 28 weight percent ammonia). One liter of distilled water was placed in a container. There was simultaneously added to the well-mixed container the two solutions from separate burets. The pH was maintained at 9.0 during the run by adjusting the flow rates. The resulting slurry was stirred for 20 minutes, then filtered and washed with ten liters of distilled water. The solids content of the filter cake was found to be 8.4 weight percent using an Ohaus moisture balance. A portion (751 grams) of the filter cake was thoroughly mixed with 42.06 grams of nickel carbonate. The resulting catalyst was oven dried at 120° C. for 18 hours, sized to 20–40 mesh and calcined at 350° C. for 10 hours. The pertinent data relating to the preparation of the catalyst used in Example I are set forth in Table III. The catalyst used in Example II was prepared following the procedure of that of Example I, except as noted in Table III.

TABLE III

| | Example No. | |
|---|---|---|
| | I | II |
| Al(NO$_3$)$_3$.9H$_2$O, g | 281.2 | 375 |
| Volume Aluminum Solution, l | 1.0 | 1.0 |
| 85% H$_3$PO$_4$, g | 28.6 | 91.5 |
| Group IIB Salt | Zn(NO$_3$)$_2$.6H$_2$O | Zn(NO$_3$)$_2$.6H$_2$O |
| Amount of Group IIB Salt, g | 74.89 | 59.5 |
| Volume of Group IIB Solution, l | 1.0 | 1.0 |
| Volume of Mixing Water, l | 1.0 | 1.0 |
| pH | 9 | 9 |
| Volume of Wash Water, l | 10 | 8 |
| Solids of Cake, Wt % | 8.4 | 16.0 |
| Weight of Cake Used, g | 751 | 711 |
| Weight of NiCO$_3$, g | 42.06 | 75.84 | the catalyst used in Example III is a proprietary catalyst sold by Harshaw Chemical Company, Cleveland, Ohio, composed of a silica based, non-phosphate-containing, support carrying 50 weight percent nickel.

The catalyst used in Example IV was prepared as follows. Forty grams of Kieselguhr (98 weight percent solids) were dry blended with 26.13 grams of nickel carbonate and then mixed with 130 cc. of distilled water. The resulting paste was dried at 120° C. for 18 hours, sized to 20–40 mesh and calcined at 350° C. for 10 hours. The resulting catalyst carried 20 weight percent nickel, as nickel oxide.

The catalyst used in Example V was prepared according to the following procedure. Forty-five grams of silica gel (94 weight percent solids), which had been sized to −100 mesh were dry blended with 28.2 grams of nickel carbonate and then mixed with 130 cc. of distilled water. The resulting paste was dried at 120° C. for 18 hours, sized to 20–40 mesh and calcined at 350° C. for 10 hours. The resulting catalyst contained 20 weight percent nickel, as nickel oxide.

The catalyst of Example VI was prepared as follows. Forty grams of alumina (85 weight percent solids) were dry blended with 22.67 grams of nickel carbonate and then mixed with 140 cc. of distilled water. The resulting paste was dried at 120° C. for 18 hours, sized to 20–40 mesh and calcined at 350° C. for 10 hours. The resulting catalyst contained 20 weight percent nickel, as nickel oxide.

Referring to Tables I and II, the "nickel utilization," we mean the weight percent of charge hydrogenated to useful and desired product per gram of elemental nickel in the catalyst. In this case, that means 2-ethyl-2-hexenal converted to the corresponding hydrogenated species, that is, a mixture of 2-ethylhexanal and 2-ethylhexanol. In each example, except Example VI, total conversion was substantially solely to a mixture of 2-ethylhexanal and 2-ethylhexanol. In Example VI, in addition to a conversion of 52 weight percent of the charge to the desired mixture, there was an additional conversion of 27 weight percent of the charge to undesired degradation and decomposition products.

The data in Tables I and II show the uniqueness of the catalysts used herein. It will be noted that in each of Examples I and II that the catalyst used herein resulted in a nickel utilization value about as high or even higher, than with nickel catalysts using conventional supports therefor. Thus, in Example III, even when a silica-based catalyst carried 50 weight percent nickel thereon, nickel utilization was only 30 and in Example IV with a Kieselguhr support, nickel utilization was but 11. In Example V with nickel on silica, a nickel utilization of 72 was achieved. While a nickel utilization of 86 was obtained with the alumina support in Example VI, as noted 27 weight percent of the charge was converted to undesired product, resulting in a selectivity of 66 percent. In each of the remaining runs we obtained 100 percent selectivity to desired product.

Special note should be taken, however, of Example I, wherein the catalyst support carrying nickel contained the Group IIB metal oxide, alumina and aluminum phosphate in the preferred ranges and the surface characteristics of the catalyst were also in the preferred ranges, nickel utilization was well above 100.

Obviously, many modifications and variations of the invention, as hereinabove set forth, can be made without departing from the spirit and scope thereof, and therefore only such limitations should be imposed as are indicated in the appended claims.

We claim:

1. A process for hydrogenating an unsaturated aliphatic organic compound having from two to 20 carbon atoms which comprises contacting the same with hydrogen in the presence of a catalyst composed of about three to about 60 weight percent nickel mounted on an amorphous support containing (1) (A) a Group IIB metal compound selected from the group consisting of zinc and cadmium compounds, (B) a combination of said zinc and cadmium compounds or (C) a combination of at least one of said Group IIB metal compounds with at least one Group IIA metal compound selected from the group consisting of magnesium, calcium, strontium and barium compounds, (2) alumina and (3) aluminum phosphate, such support having an average pore radius of from about 10 Å to about 300 Å, a surface area ranging from about 80 m$^2$/g to about 350 m$^2$/g and a pore volume of from about 0.3 cc/g to about 1.5 cc/g, said Group IIB, and IIA, when present, metal compound being present in an amount ranging from about two to about 35 mole percent, alumina in an amount ranging from about 15 to about 60 mole percent and aluminum phosphate in an amount ranging from about 2.5 to about 80 mole percent, wherein said unsaturated organic compound is passed over said catalyst at a liquid hourly space velocity of about 0.1 to about 20 while maintaining in the reaction zone a temperature of about 30° to about 350° C. and a hydrogen partial pressure of about 0 to about 1500 pounds per square inch gauge.

2. The process of claim 1 wherein said support has an average pore radius of from about 50 Å to about 200 Å, a surface area of about 125 m$^2$/g to about 250 m$^2$/g and a pore volume of from about 0.5 cc/g to about 1.2 cc/g.

3. The process of claim 1 wherein said Group IIB metal compound is a Group IIB metal oxide.

4. The process of claim 2 wherein said Group IIB metal compound is a Group IIB metal oxide.

5. The process of claim 1 wherein said Group IIB metal compound is zinc oxide.

6. The process of claim 2 wherein said Group IIB metal compound is zinc oxide.

7. The process of claim 1 wherein said Group IIB metal compound is cadmium oxide.

8. The process of claim 2 wherein said Group IIB metal compound is cadmium oxide.

9. The process of claim 1 wherein said Group IIB metal component includes zinc and magnesium oxides.

10. The process of claim 2 wherein said Group IIB metal component includes zinc and magnesium oxides.

11. The process of claim 1 wherein said Group IIB metal component includes zinc and calcium oxides.

12. The process of claim 2 wherein said Group IIB metal component includes zinc and calcium oxides.

13. The process of claim 2 wherein the amount of nickel carried on said support is in the range of about five to about 25 weight percent.

14. The process of claim 2 wherein said unsaturated organic compound is passed over said catalyst at a liquid hourly space velocity of about 1 to about 12, while maintaining in the reaction zone a temperature of about 50° to about 200° C. and a hydrogen partial pressure of about 100 to about 500 pounds per square inch gauge.

15. The process of claim 2 wherein said unsaturated organic compound is an aliphatic compound having from two to 12 carbon atoms.

16. The process of claim 1 wherein said unsaturated organic compound is an unsaturated aldehyde.

17. The process of claim 2 wherein said unsaturated organic compound is an unsaturated aldehyde.

18. The process of claim 1 wherein said unsaturated organic compound is 2-ethyl-2-hexenal.

19. The process of claim 2 wherein said unsaturated organic compound is 2-ethyl-2-hexenal.

* * * * *

UNITED STATES PATENT OFFICE
CERTIFICATE OF CORRECTION

Patent No. 4,365,095          Dated December 21, 1982

Inventor(s) George Marcelin, Roger F. Vogel, Harold E. Swift

It is certified that error appears in the above-identified patent and that said Letters Patent are hereby corrected as shown below:

Column 2, lines 2 and 3, delete after "about", the following "250 $m^2$/g, and a pore volume of from about 0.3 cc/g to about".

Column 2, line 4, "250 $^2$/g" should read --250 $m^2$/g--.

Column 2, line 5, after "volume" delete "o" and insert --of--.

Signed and Sealed this

Twelfth Day of April 1983

[SEAL]

Attest:

GERALD J. MOSSINGHOFF

Attesting Officer     Commissioner of Patents and Trademarks